(12) United States Patent
Tsumaki et al.

(10) Patent No.: US 9,668,985 B2
(45) Date of Patent: Jun. 6, 2017

(54) PTEROSIN DERIVATIVE-CONTAINING THERAPEUTIC PREPARATION FOR DISEASE ASSOCIATED WITH CARTILAGE LOSS, CARTILAGE DEGENERATION AND/OR CARTILAGE THINNING

(71) Applicant: KYOTO UNIVERSITY

(72) Inventors: Noriyuki Tsumaki, Kyoto (JP); Hiroshi Takemori, Osaka (JP); Hiroyuki Fuchino, Ibaraki (JP); Nobuo Kawahara, Ibaraki (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 14/315,809

(22) Filed: Oct. 14, 2014

(65) Prior Publication Data

US 2015/0051293 A1    Feb. 19, 2015

(30) Foreign Application Priority Data

Jun. 27, 2013 (JP) ................................ 2013-135040

(51) Int. Cl.
*A01N 47/34* (2006.01)
*A61K 31/175* (2006.01)
*A61K 31/122* (2006.01)

(52) U.S. Cl.
CPC .................. *A61K 31/122* (2013.01)

(58) Field of Classification Search
CPC .................. C07C 49/513; C07C 49/517
See application file for complete search history.

(56) References Cited

FOREIGN PATENT DOCUMENTS

| JP | 2002-51786 | 2/2002 |
| WO | WO 03099795 A1 * | 12/2003 |
| WO | 2010/046443 | 4/2010 |
| WO | 2012/165407 | 12/2012 |

OTHER PUBLICATIONS

Wu et al, Journal of Ethnopharmacology 98 (2005) 73-81.*
Chen et al, Molecules 2008, 13, 255-266.*
Habtemariam, Phytopharmacology 2013, 4(1), 131-148.*
Yahara et al, Nature Communications, published in Mar. 2016.*
International Search Report issued Aug. 14, 2012 in International (PCT) Application No. PCT/JP2012/063709.
Lin et al., "Modulating hedgehog signaling can attenuate the severity of osteoarthritis", Nature Medicine, vol. 15, No. 12, Dec. 2009, pp. 1421-1425.
Saito et al., "Transcriptional regulation of endochondral ossification by HIF-2α during skeletal growth and osteoarthritis development", Nature Medicine, vol. 16, No. 6, Jun. 2010, pp. 678-686.
Yang et al., "Hypoxia-inducible factor-2α is a catabolic regulator of osteoarthritic cartilage destruction", Nature Medicine, vol. 16, No. 6, Jun. 2010, pp. 687-693.
Yuasa et al., "Transient Activation of Wnt/β-Catenin Signaling Induces Abnormal Growth Plate Closure and Articular Cartilage Thickening in Postnatal Mice", The American Journal of Pathology, vol. 175, No. 5, Nov. 2009, pp. 1993-2003.
Pelttari et al., "Premature Induction of Hypertrophy During In Vitro Chondrogenesis of Human Mesenchymal Stem Cells Correlates With Calcification and Vascular Invasion After Ectopic Transplantation in SCID Mice", Arthritis & Rheumatism, vol. 54, No. 10, Oct. 2006, pp. 3254-3266.
Warman et al., "Nosology and Classification of Genetic Skeletal Disorders: 2010 Revision", American Journal of Medical Genetics, vol. 155, No. 5, May 2011, pp. 943-968.

* cited by examiner

*Primary Examiner* — Jean Cornet
(74) *Attorney, Agent, or Firm* — Wenderoth, Lind & Ponack, L.L.P.

(57) ABSTRACT

An object of the present invention is to provide a therapeutic preparation and method for diseases associated with cartilage loss, cartilage degeneration and/or cartilage thinning. The present invention provides a therapeutic preparation comprising a pterosin derivative or a pharmaceutically acceptable salt thereof for diseases associated with cartilage loss, cartilage degeneration and/or cartilage thinning; and a therapeutic method for the diseases.

2 Claims, 8 Drawing Sheets

** : vs DMSO P < 0.01  Tukey-Kramer

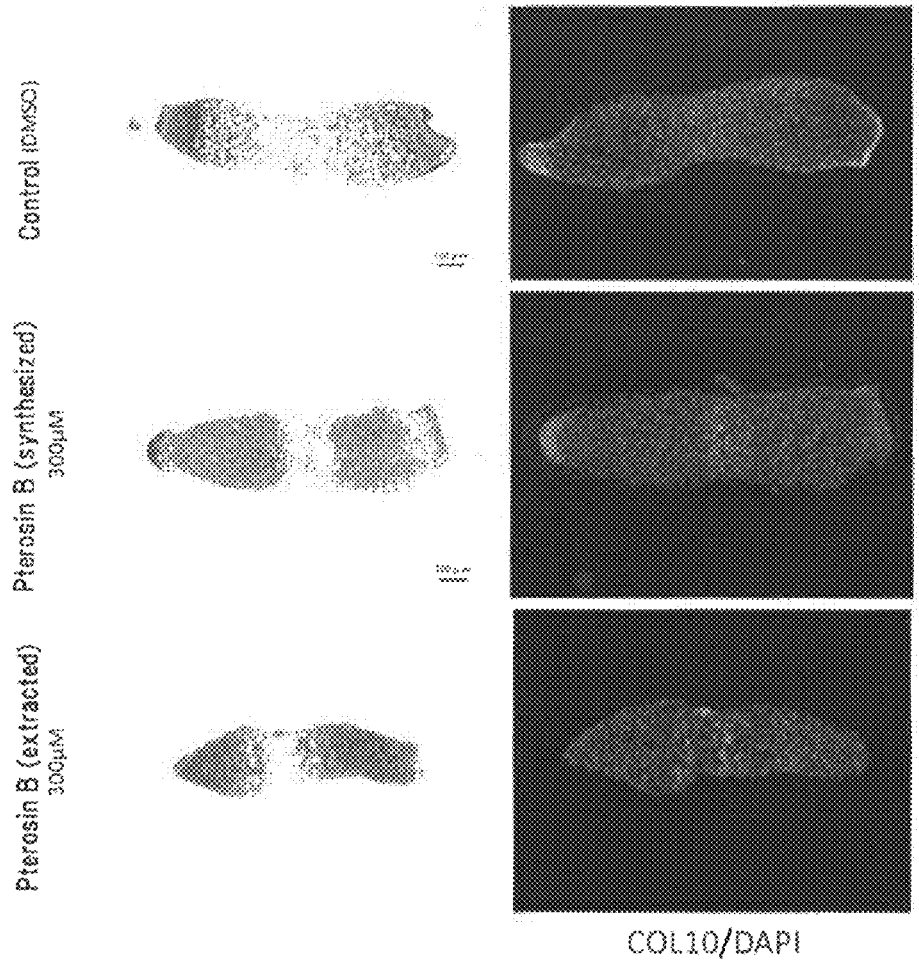

✓ Day3
✓ DMEM + 10% FBS

Cell growth in 7-day monolayer culture

Pellet culture

Fig. 7A
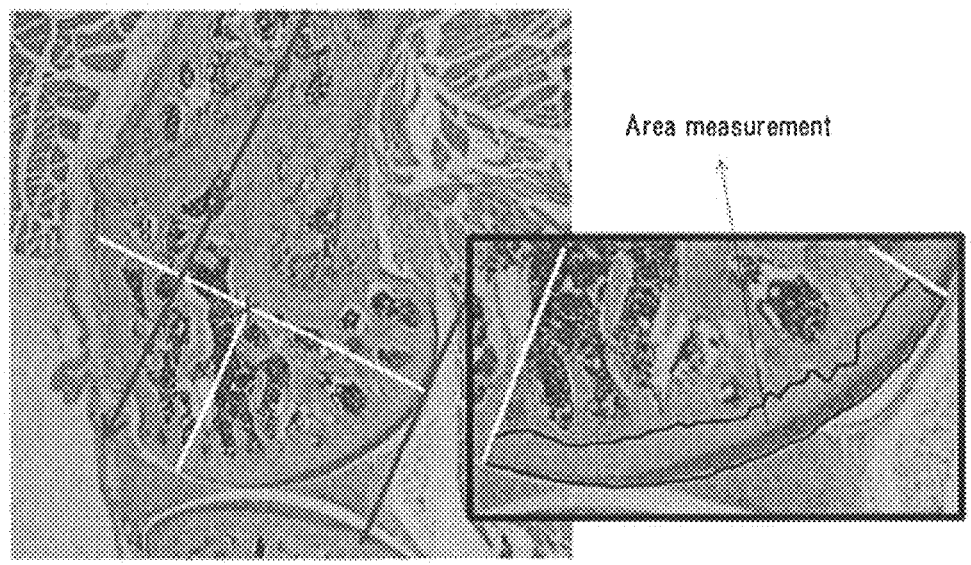
Area measurement
Fig. 7B
DMSO-PBS
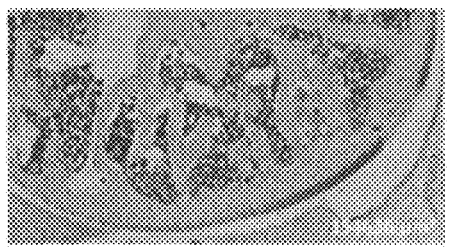
Pterosin B 900μM
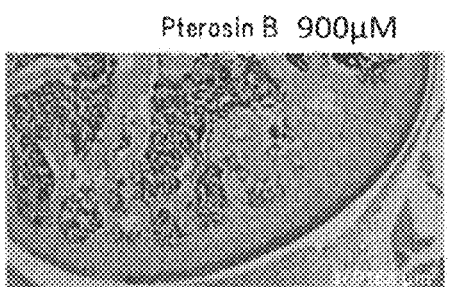
Fig. 7C
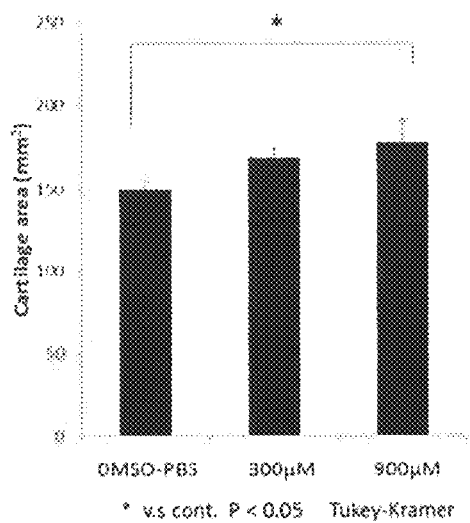
Cartilage area of medial epicondyle
* v.s cont. P < 0.05   Tukey-Kramer

PTEROSIN DERIVATIVE-CONTAINING THERAPEUTIC PREPARATION FOR DISEASE ASSOCIATED WITH CARTILAGE LOSS, CARTILAGE DEGENERATION AND/OR CARTILAGE THINNING

TECHNICAL FIELD

The present invention relates to a therapeutic preparation, a pharmaceutical composition and a functional food that are useful for the treatment of a disease associated with cartilage loss, cartilage degeneration and/or cartilage thinning; and a method for treating the disease using the therapeutic preparation (or the pharmaceutical composition).

BACKGROUND ART

Articular cartilage covers bone surfaces in diarthrodial joints and is composed of cartilage matrices and a small amount of chondrocytes. Articular cartilage has little blood flow, and thus it is usually said that articular cartilage, once degenerated or lost, can hardly be repaired. Diseases associated with loss or degeneration of articular cartilage are, for example, traumatic chondropathy, rheumatoid arthritis, osteoarthritis, etc. In addition, articular cartilage thins with aging.

Osteoarthritis is a progressive degenerative arthritis characterized by articular cartilage degeneration, and subchondral bone growth and remodeling. The disease presents with symptoms such as stiffness, movement limitation and pain, and increases in incidence with age. However, there is no treatment for radical cure of osteoarthritis because cartilage has a limited self renewal capacity, and the current treatment of osteoarthritis is to control pain by exercise restriction and painkiller medication. In the case where the disease has progressed into the terminal phase, joint arthroplasty, which is a surgery involving excising degenerated articular cartilage and resurfacing the bone with a metal cover, is a treatment option.

For the development of cartilage repair promoting agents, screening for compounds and proteins promoting chondrocyte growth has been carried out, and SIK3-inhibiting compounds have been reported to be a candidate (Patent Literature 1). Further, bone morphogenetic proteins (BMPs) are known to be capable of actually promoting cartilage growth at the tissue level. However, BMPs, after inducing cartilage growth, induce hypertrophic differentiation of chondrocytes, resulting in the replacement of cartilage by bone. Due to the action, it is problematic to use BMPs for the treatment of articular cartilage defects. In recent years, it has been suggested that promotion of chondrocyte hypertrophy is involved in articular cartilage degeneration, and preventing chondrocyte hypertrophy is a major therapeutic target for osteoarthritis. The target molecules identified so far include Hedgehog (Non Patent Literature 1) and Hif-2α (Non Patent Literature 2 and 3). It is also reported that transient activation of β-catenin signaling induces articular cartilage thickening (Non Patent Literature 4).

For the treatment of articular cartilage injuries and growth cartilage injuries caused by trauma, blood circulation failure, etc., regenerative medicine using transplantation of stem cell-derived cells has been studied. However, chondrocyte-like cells derived from stem cells tend to undergo hypertrophy, which poses a problem (Non Patent Literature 5).

CITATION LIST

Patent Literature

Patent Literature 1: WO 2012165407

Non Patent Literature

Non Patent Literature 1:
Lin A C et al., Nat Med. 2009; 15: 1421-1425.
Non Patent Literature 2:
Saito T et al., Nat Med. 2010; 16: 678-686.
Non Patent Literature 3:
Yang S et al., Nat Med. 2010; 16: 687-693.
Non Patent Literature 4:
Yuasa T et al., Am J Pathol. 2009; 175: 1993-2003.
Non Patent Literature 5:
Pelttari K et al., Arthritis Rheum. 2006; 54: 3254-3266.

SUMMARY OF INVENTION

Technical Problem

An object of the present invention is to provide a novel therapeutic preparation, a novel pharmaceutical composition and a novel functional food that are used for a disease associated with cartilage loss, cartilage degeneration and/or cartilage thinning; and a method for treating the disease using the therapeutic preparation (or the pharmaceutical composition).

Solution to Problem

The present inventors conducted intensive research using numerous compounds to achieve the above-mentioned object, and as a result, found that pterosin derivatives surprisingly have the effects to promote chondrocyte growth and cartilage matrix production and to inhibit chondrocyte hypertrophy. Based on these findings, the present inventors conducted further research and completed the present invention.

That is, the present invention includes the following.
[1] A therapeutic preparation for a disease associated with cartilage loss, cartilage degeneration and/or cartilage thinning, comprising a pterosin derivative represented by formula (I):

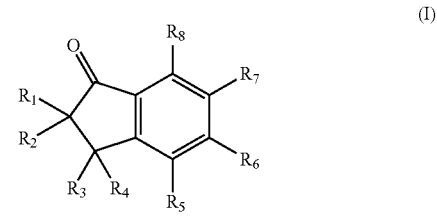

(wherein $R_1$, $R_2$, $R_3$, $R_4$, $R_5$, $R_6$, $R_7$ and $R_8$ are independently hydrogen, a hydroxy group, an amino group, a halogen group, an alkyl group, an alkenyl group, an alkynyl group, a cycloalkyl group, a heterocycloalkyl group, an aryl group, a heteroaryl group, an alkoxy group, an alkoxycarbonyl group, an acyloxy group, an alkylthio group, an alkylamino group, a glycosyl group, a glycosyloxy group or a glucosyloxy alkyl group; and the amino group, the alkyl group, the alkenyl group, the alkynyl group, the cycloalkyl group, the heterocycloalkyl group, the aryl group, the heteroaryl group, the alkoxy group, the alkoxycarbonyl group, the acyloxy group, the alkylthio group and the alkylamino group optionally have a substituent;

$R_5$, $R_6$ and the two carbon atoms bound to $R_5$ and $R_6$ may join together to form a 5- to 8-membered ring having one, two or three heteroatoms;

$R_6$, $R_7$ and the two carbon atoms bound to $R_6$ and $R_7$ may join together to form a 5- to 8-membered ring having one, two or three heteroatoms;

$R_7$, $R_8$ and the two carbon atoms bound to $R_7$ and $R_8$ may join together to form a 5- to 8-membered ring having one, two or three heteroatoms; and $R_3$ and $R_4$ are not hydroxy groups)

or a pharmaceutically acceptable salt thereof.

[2] The therapeutic preparation according to the above [1], wherein the pterosin derivative is a compound represented by formula (II):

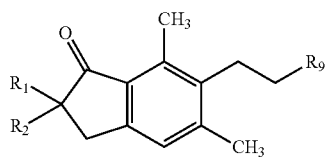

(II)

or formula (III):

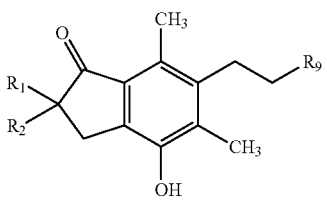

(III)

(wherein $R_1$ and $R_2$ are independently hydrogen, a hydroxy group, an amino group, a halogen group, an alkyl group, an alkenyl group, an alkynyl group, a cycloalkyl group, a heterocycloalkyl group, an aryl group, a heteroaryl group, an alkoxy group, an alkoxycarbonyl group, an acyloxy group, an alkylthio group, an alkylamino group, a glycosyl group, a glycosyloxy group or a glucosyloxy alkyl group; and $R_9$ is hydrogen, a hydroxy group, a carboxyl group, an amino group, a halogen group, an alkoxy group, an alkoxycarbonyl group, an acyloxy group, an alkylthio group, an alkylamino group, a glycosyl group or a glycosyloxy group).

[3] The therapeutic preparation according to the above [1] or [2], wherein the pterosin derivative is a compound represented by formula (II) or (III) wherein $R_1$ and $R_2$ are independently hydrogen, a methyl group or a hydroxymethyl group, and $R_9$ is a hydroxy group, a methoxy group or chlorine.

[4] The therapeutic preparation according to any one of the above [1] to [3], wherein the pterosin derivative is a compound represented by formula (IV):

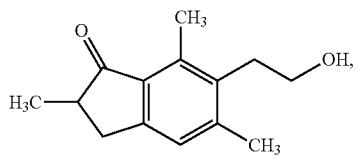

(IV)

formula (V):

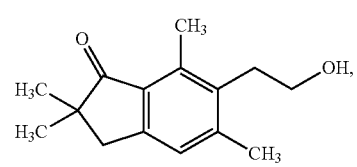

(V)

formula (VI):

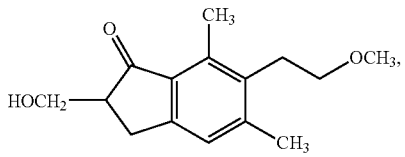

(VI)

formula (VII):

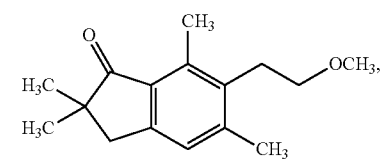

(VII)

formula (VIII):

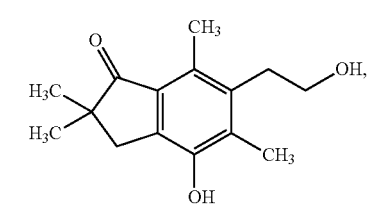

(VIII)

formula (IX):

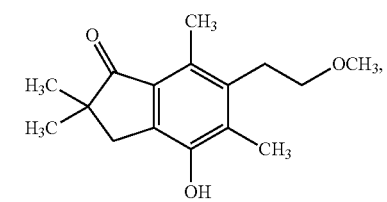

(IX)

or formula (X):

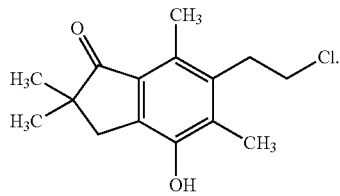

[5] The therapeutic preparation according to any one of the above [1] to [4], wherein the disease associated with cartilage loss, cartilage degeneration and/or cartilage thinning is osteoarthritis.

[6] A functional food for treatment of a disease associated with cartilage loss, cartilage degeneration and/or cartilage thinning, comprising a pterosin derivative represented by formula (I):

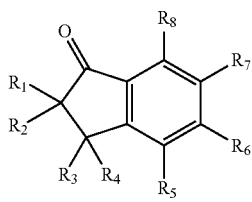

(wherein $R_1$, $R_2$, $R_3$, $R_4$, $R_5$, $R_6$, $R_7$ and $R_8$ are independently hydrogen, a hydroxy group, an amino group, a halogen group, an alkyl group, an alkenyl group, an alkynyl group, a cycloalkyl group, a heterocycloalkyl group, an aryl group, a heteroaryl group, an alkoxy group, an alkoxycarbonyl group, an acyloxy group, an alkylthio group, an alkylamino group, a glycosyl group, a glycosyloxy group or a glucosyloxy alkyl group; and the amino group, the alkyl group, the alkenyl group, the alkynyl group, the cycloalkyl group, the heterocycloalkyl group, the aryl group, the heteroaryl group, the alkoxy group, the alkoxycarbonyl group, the acyloxy group, the alkylthio group and the alkylamino group optionally have a substituent;

$R_5$, $R_6$ and the two carbon atoms bound to $R_5$ and $R_6$ may join together to form a 5- to 8-membered ring having one, two or three heteroatoms;

$R_6$, $R_7$ and the two carbon atoms bound to $R_6$ and $R_7$ may join together to form a 5- to 8-membered ring having one, two or three heteroatoms;

$R_7$, $R_8$ and the two carbon atoms bound to $R_7$ and $R_8$ may join together to form a 5- to 8-membered ring having one, two or three heteroatoms; and $R_3$ and $R_4$ are not hydroxy groups)

or a pharmaceutically acceptable salt thereof.

[7] The functional food according to the above [6], wherein the pterosin derivative is a compound represented by formula (II):

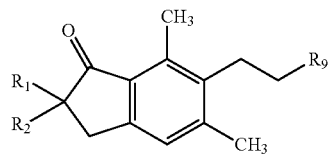

or formula (III):

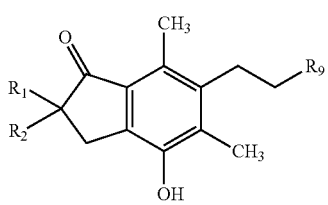

(wherein $R_1$ and $R_2$ are independently hydrogen, a hydroxy group, an amino group, a halogen group, an alkyl group, an alkenyl group, an alkynyl group, a cycloalkyl group, a heterocycloalkyl group, an aryl group, a heteroaryl group, an alkoxy group, an alkoxycarbonyl group, an acyloxy group, an alkylthio group, an alkylamino group, a glycosyl group, a glycosyloxy group or a glucosyloxy alkyl group; and $R_9$ is hydrogen, a hydroxy group, a carboxyl group, an amino group, a halogen group, an alkoxy group, an alkoxycarbonyl group, an acyloxy group, an alkylthio group, an alkylamino group, a glycosyl group or a glycosyloxy group).

[8] The functional food according to the above [6] or [7], wherein the pterosin derivative is a compound represented by formula (II) or (III) wherein $R_1$ and $R_2$ are independently hydrogen, a methyl group or a hydroxymethyl group, and $R_9$ is a hydroxy group, a methoxy group or chlorine.

[9] The functional food according to any one of the above [6] to [8], wherein the pterosin derivative is a compound represented by formula (IV):

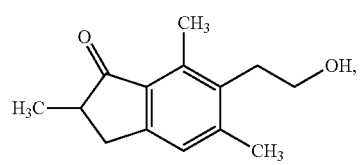

formula (V):

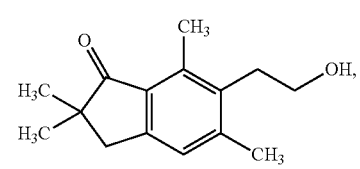

formula (VI):

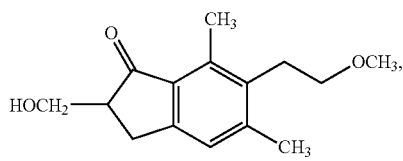

formula (VII):

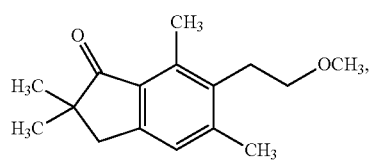

formula (VIII):

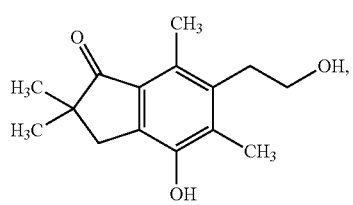

formula (IX):

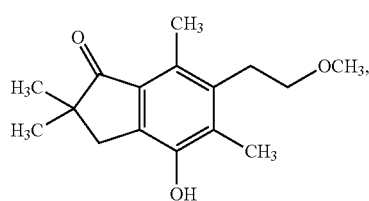

or formula (X):

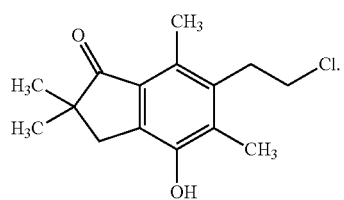

[10] The functional food according to any one of the above [6] to [9], wherein the disease associated with cartilage loss, cartilage degeneration and/or cartilage thinning is osteoarthritis.

[11] A method for preventing and/or treating a disease associated with cartilage loss, cartilage degeneration and/or cartilage thinning, comprising the step of administering a pterosin derivative represented by formula (I):

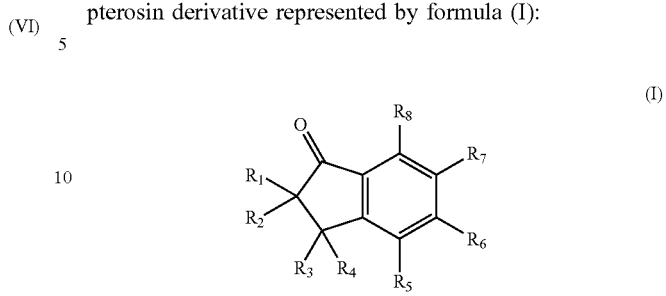

(wherein $R_1$, $R_2$, $R_3$, $R_4$, $R_5$, $R_6$, $R_7$ and $R_8$ are independently hydrogen, a hydroxy group, an amino group, a halogen group, an alkyl group, an alkenyl group, an alkynyl group, a cycloalkyl group, a heterocycloalkyl group, an aryl group, a heteroaryl group, an alkoxy group, an alkoxycarbonyl group, an acyloxy group, an alkylthio group, an alkylamino group, a glycosyl group, a glycosyloxy group or a glucosyloxy alkyl group; and the amino group, the alkyl group, the alkenyl group, the alkynyl group, the cycloalkyl group, the heterocycloalkyl group, the aryl group, the heteroaryl group, the alkoxy group, the alkoxycarbonyl group, the acyloxy group, the alkylthio group and the alkylamino group optionally have a substituent;

$R_5$, $R_6$ and the two carbon atoms bound to $R_5$ and $R_6$ may join together to form a 5- to 8-membered ring having one, two or three heteroatoms;

$R_6$, $R_7$ and the two carbon atoms bound to $R_6$ and $R_7$ may join together to form a 5- to 8-membered ring having one, two or three heteroatoms;

$R_7$, $R_8$ and the two carbon atoms bound to $R_7$ and $R_8$ may join together to form a 5- to 8-membered ring having one, two or three heteroatoms; and $R_3$ and $R_4$ are not hydroxy groups)

or a pharmaceutically acceptable salt thereof (or a pharmaceutical composition comprising the pterosin derivative or a pharmaceutically acceptable salt thereof) to a patient.

[12] The method according to the above [11], wherein the pterosin derivative is a compound represented by formula (II):

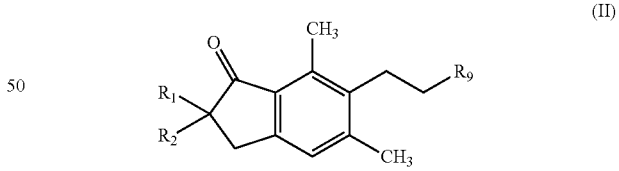

or formula (III):

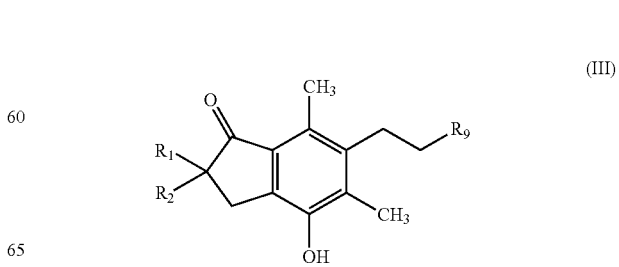

(wherein $R_1$ and $R_2$ are independently hydrogen, a hydroxy group, an amino group, a halogen group, an alkyl group, an alkenyl group, an alkynyl group, a cycloalkyl group, a heterocycloalkyl group, an aryl group, a heteroaryl group, an alkoxy group, an alkoxycarbonyl group, an acyloxy group, an alkylthio group, an alkylamino group, a glycosyl group, a glycosyloxy group or a glucosyloxy alkyl group; and $R_9$ is hydrogen, a hydroxy group, a carboxyl group, an amino group, a halogen group, an alkoxy group, an alkoxycarbonyl group, an acyloxy group, an alkylthio group, an alkylamino group, a glycosyl group or a glycosyloxy group).

[13] The method according to the above [11] or [12], wherein the pterosin derivative is a compound represented by formula (II) or (III) wherein $R_1$ and $R_2$ are independently hydrogen, a methyl group or a hydroxymethyl group, and $R_9$ is a hydroxy group, a methoxy group or chlorine.

[14] The method according to any one of the above [11] to [13], wherein the pterosin derivative is a compound represented by formula (IV):

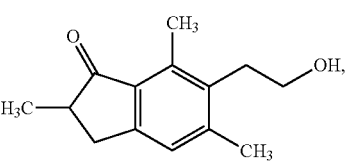

(IV)

formula (V):

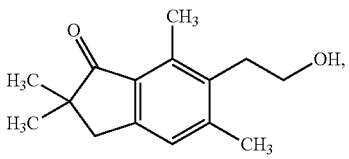

(V)

formula (VI):

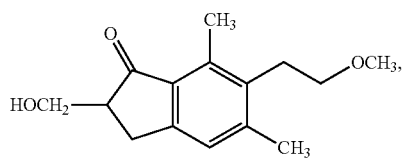

(VI)

formula (VII):

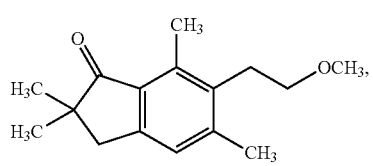

(VII)

formula (VIII):

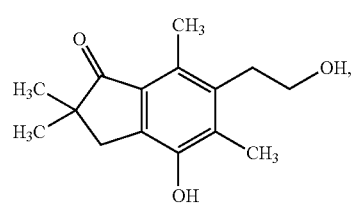

(VIII)

formula (IX):

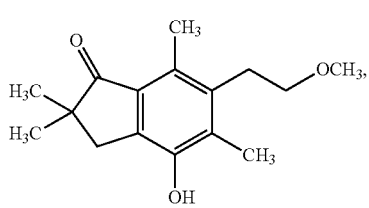

(IX)

or formula (X):

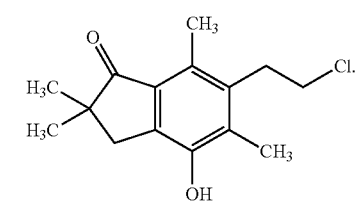

(X)

[15] The method according to any one of the above [11] to [14], wherein the disease associated with cartilage loss, cartilage degeneration and/or cartilage thinning is osteoarthritis.

Advantageous Effects of Invention

According to the present invention, pterosin derivatives have the effects to promote chondrocyte growth and cartilage matrix production and to inhibit chondrocyte hypertrophy, and therefore are applicable as a therapeutic preparation for administration to a patient with a disease associated with cartilage loss, cartilage degeneration and/or cartilage thinning.

BRIEF DESCRIPTION OF DRAWINGS

FIG. 4 shows typical images of Col10a1 staining and DAPI staining in embryonic mouse metatarsal bone tissue-cultured in the presence of a vehicle control (DMSO), synthesized pterosin B or extracted pterosin B.

FIG. 7A shows the method for measuring the area of articular cartilage.

FIG. 7B shows images of safranin O immunostaining in joints after 4-week intra-articular administration of a control (DMSO) or pterosin B.

FIG. 7C shows the measured area of articular cartilage after 4-week intra-articular administration of a control (DMSO) or pterosin B.

DESCRIPTION OF EMBODIMENTS

Figure 1A:
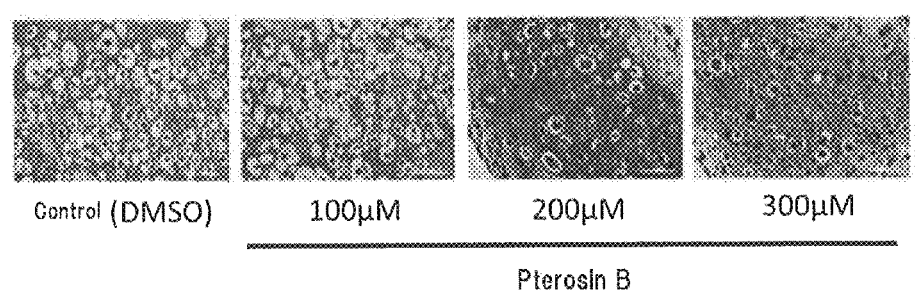
FIG. 1A shows images of safranin O staining in wild-type mouse primary chondrocytes pellet-cultured in the presence of a vehicle control (DMSO) or various concentrations of pterosin B.

The present invention provides a therapeutic preparation and a pharmaceutical composition each comprising a pterosin derivative for the treatment of a disease associated with cartilage loss, cartilage degeneration and/or cartilage thinning.

In the present invention, the disease associated with cartilage loss, cartilage degeneration and/or cartilage thinning is a pathological condition in which the cartilage of a joint has been lost, degenerated and/or thinned due to trauma, autoimmunity, aging, etc., and is exemplified by traumatic chondropathy (for example, osteochondritis dissecans), rheumatoid arthritis, osteoarthritis, etc. Considering the effects of the pterosin derivative of the present invention, a preferred pathological condition is not complete loss of cartilage, but partial loss of cartilage and cartilage matrices. More preferred is osteoarthritis, and further preferred is knee osteoarthritis. Also preferred is age-related thinning of articular cartilage.

In the present invention, the pterosin derivative is, for example, a compound defined in WO2010/085811, and more particularly, a compound represented by formula (I):

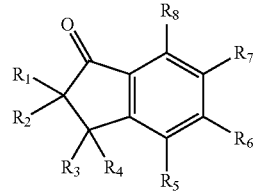

wherein $R_1$, $R_2$, $R_3$, $R_4$, $R_5$, $R_6$, $R_7$ and $R_8$ are independently hydrogen, a hydroxy group, an amino group, a halogen group, an alkyl group, an alkenyl group, an alkynyl group, a cycloalkyl group, a heterocycloalkyl group, an aryl group, a heteroaryl group, an alkoxy group, an alkoxycarbonyl group, an acyloxy group, an alkylthio group, an alkylamino group, a glycosyl group, a glycosyloxy group or a glucosyloxy alkyl group; and the amino group, the alkyl group, the alkenyl group, the alkynyl group, the cycloalkyl group, the heterocycloalkyl group, the aryl group, the heteroaryl group, the alkoxy group, the alkoxycarbonyl group, the acyloxy group, the alkylthio group and the alkylamino group optionally have a substituent (a substituent mentioned below, etc.);

$R_5$, $R_6$ and the two carbon atoms bound to $R_5$ and $R_6$ may join together to form a 5- to 8-membered ring having one, two or three heteroatoms;

$R_6$, $R_7$ and the two carbon atoms bound to $R_6$ and $R_7$ may join together to form a 5- to 8-membered ring having one, two or three heteroatoms; and $R_7$, $R_8$ and the two carbon atoms bound to $R_7$ and $R_8$ may join together to form a 5- to 8-membered ring having one, two or three heteroatoms.

Any two groups selected from the group consisting of $R_1$, $R_2$, $R_3$ and $R_4$ may join together with the carbon atom(s) bound to the two groups to form a 3- to 8-membered ring. Any two groups selected from the group consisting of $R_5$, $R_6$, $R_7$ and $R_8$ may join together with the carbon atoms bound to the two groups to form a 3- to 8-membered ring. When constituting a ring, $R_1$, $R_2$, $R_3$, $R_4$, $R_5$, $R_6$, $R_7$ and $R_8$ may be alkylene groups.

In the above formula (I), $R_3$ and $R_4$ are typically not hydroxy groups. Particularly, a compound of the above formula (I) in which $R_3$ and $R_4$ are hydrogen atoms, that is, $R_3$ and $R_4$ are unoccupied by substituents (for example, a compound represented by formula (II) or (III) shown below) may preferably be used in the present invention.

In the present invention, a preferable pterosin derivative is a compound of formula (I) in which $R_3$, $R_4$ and $R_5$ are hydrogen atoms, and $R_6$ and $R_8$ are methyl groups, as represented by formula (II):

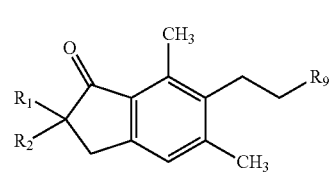

or a compound of formula (I) in which $R_3$ and $R_4$ are hydrogen atoms, $R_5$ is a hydroxy group, and $R_6$ and $R_8$ are methyl groups, as represented by formula (III):

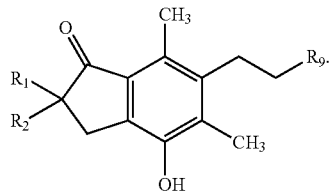

(III)

In both formulae, $R_9$ is hydrogen, a hydroxy group, a carboxyl group, an amino group, a halogen group, an alkoxy group, an alkoxycarbonyl group, an acyloxy group, an alkylthio group, an alkylamino group, a glycosyl group or a glycosyloxy group.

A more preferable pterosin derivative is a compound of formula (II) or (III) in which $R_1$ and $R_2$ are independently hydrogen, a methyl group or a hydroxymethyl group, and $R_9$ is a hydroxy group, a methoxy group or chlorine.

A most preferable pterosin derivative is a compound of formula (II) in which $R_1$ is a methyl group, $R_2$ is hydrogen, and $R_9$ is a hydroxy group, namely, pterosin B, which is represented by formula (IV):

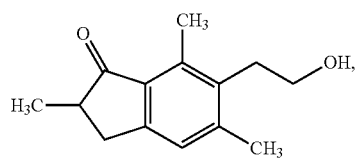

(IV)

a compound of formula (II) in which $R_1$ is a methyl group, $R_2$ is a methyl group, and $R_9$ is a hydroxy group, namely, pterosin Z, which is represented by formula (V):

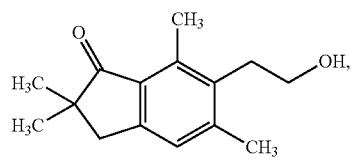

(V)

a compound of formula (II) in which $R_1$ is a hydroxymethyl group, $R_2$ is hydrogen, and $R_9$ is a methoxy group, namely, 14-O-methylpterosin G, which is represented by formula (VI):

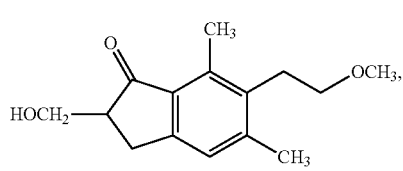

(VI)

a compound of formula (II) in which $R_1$ is a methyl group, $R_2$ is a methyl group, and $R_9$ is a methoxy group, namely, pterosin I, which is represented by formula (VII):

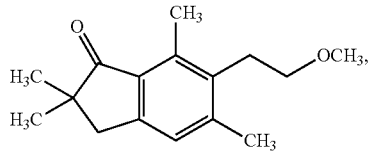

(VII)

a compound of formula (III) in which $R_1$ is a methyl group, $R_2$ is a methyl group, and $R_9$ is a hydroxy group, namely, onitin, which is represented by formula (VIII):

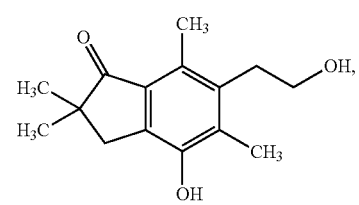

(VIII)

a compound of formula (III) in which $R_1$ is a methyl group, $R_2$ is a methyl group, and $R_9$ is a methoxy group, namely, 14-O-methylonitin, which is represented by formula (IX):

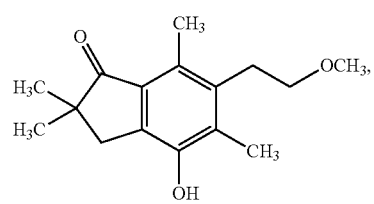

(IX)

or a compound of formula (III) in which $R_1$ is a methyl group, $R_2$ is a methyl group, and $R_9$ is a methoxy group, namely, 14-deoxy-14-chloroonitin (or pterosin R), which is represented by formula (X):

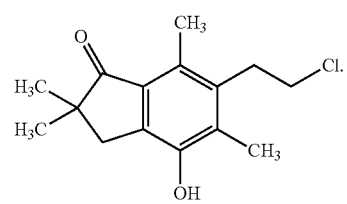

(X)

The alkyl group as used herein refers to a straight or branched monovalent hydrocarbon having 1 to 20 carbon atoms (for example, C1 to C8) unless otherwise specified. Examples of the alkyl group include, but are not limited to, a methyl group, an ethyl group, a n-propyl group, an i-propyl group, a n-butyl group, an i-butyl group and a t-butyl group.

The alkylene group as used herein refers to a straight or branched divalent hydrocarbon having 1 to 20 carbon atoms (for example, C1 to C8). Examples of the alkylene group include, but are not limited to, a methylene group and an ethylene group.

The alkenyl group as used herein refers to a straight or branched, monovalent or divalent hydrocarbon having 2 to 20 carbon atoms (for example, C2 to C10) and one or more double bonds. Examples of the alkenyl group include, but are not limited to, an ethenyl group, a propenyl group, a propenylene group, an allyl group and a 1,4-butadienyl group.

The alkynyl group as used herein refers to a straight or branched, monovalent or divalent hydrocarbon having 2 to 20 carbon atoms (for example, C2 to C10) and one or more triple bonds. Examples of the alkynyl group include, but are not limited to, an ethynyl group, an ethynylene group, a 1-propynyl group, a 1-butynyl group, a 2-butynyl group and a 1-methyl-2-butynyl group.

The cycloalkyl group as used herein refers to a monovalent or divalent saturated hydrocarbon ring system having 3 to 30 carbon atoms (for example, C3 to C12). Examples of the cycloalkyl group include, but are not limited to, a cyclopropyl group, a cyclobutyl group, a cyclopentyl group, a cyclohexyl group, a 1,4-cyclohexylene group, a cycloheptyl group, a cyclooctyl group and an adamantyl group.

The heterocycloalkyl group as used herein refers to a monovalent or divalent, 5- to 8-membered monocyclic, 8- to 12-membered bicyclic or 11- to 14-membered tricyclic non-aromatic ring system having one or more heteroatoms (O, N, S, Se, etc.). Examples of the heterocycloalkyl group include, but are not limited to, a piperazinyl group, a pyrrolidinyl group, a dioxanyl group, a morpholinyl group and a tetrahydrofuranyl group.

The aryl group as used herein refers to a monovalent 6-membered monocyclic, 10-membered bicyclic or 14-membered tricyclic carboaromatic ring system. Examples of the aryl group include, but are not limited to, a phenyl group, a naphthyl group and an anthracenyl group.

The heteroaryl group as used herein refers to a monovalent 5- to 8-membered monocyclic, 8- to 12-membered bicyclic or 11- to 14-membered tricyclic aromatic ring system having one or more heteroatoms (O, N, S, Se, etc.). Example of the heteroaryl group include a pyridyl group, a furyl group, an imidazolyl group, a benzimidazolyl group, a pyrimidinyl group, a thienyl group, a quinolinyl group, an indolyl group and a thiazolyl group.

The alkoxy group as used herein refers to a —O—R group in which R can be an alkyl group, an alkenyl group, an alkynyl group, a cycloalkyl group, a cycloalkenyl group, a heterocycloalkyl group, an aryl group or a heteroaryl group.

The alkylthio group as used herein refers to a —S—R group in which R can be an alkyl group, an alkenyl group, an alkynyl group, a cycloalkyl group, a cycloalkenyl group, a heterocycloalkyl group, an aryl group or a heteroaryl group.

The alkylamino group as used herein refers to a —N—(R)$_2$ group in which R can be hydrogen, an alkyl group, an alkenyl group, an alkynyl group, a cycloalkyl group, a cycloalkenyl group, a heterocycloalkyl group, an aryl group or a heteroaryl group.

The alkoxycarbonyl group as used herein refers to a —C(O)—O—R group in which R can be hydrogen, an alkyl group, an alkenyl group, an alkynyl group, a cycloalkyl group, a cycloalkenyl group, a heterocycloalkyl group, an aryl group or a heteroaryl group.

The acyloxy group as used herein refers to a —O—C(O)—R group in which R can be an alkyl group, an alkenyl group, an alkynyl group, a cycloalkyl group, a cycloalkenyl group, a heterocycloalkyl group, an aryl group or a heteroaryl group.

The glycosyl group as used herein refers to a monosaccharide residue, and the examples include ribosyl, lyxosyl, xylosyl, arabinosyl, allopyranosyl, talopyranosyl, glucopyranosyl, altropyranosyl, mannopyranosyl and galactopyranosyl. The configuration of the glycosidic linkage can be an α or β configuration depending on the stereochemistry of constituent monosaccharides, and thus both D isomers and L isomers are included in the present invention.

The glycosyloxy group as used herein refers to a —O-glycosyl group, and the examples include ribosyloxy, lyxosyloxy, xylosyloxy, arabinopyranosyloxy, allopyranosyloxy, talopyranosyloxy, glucopyranosyloxy, altropyranosyloxy, mannopyranosyloxy and galactopyranosyloxy. The configuration of the glycosidic linkage can be an α or β configuration depending on the stereochemistry of constituent monosaccharides, and thus both isomers are included in the present invention.

The glucosyloxy alkyl group as used herein refers to a —R—O-glycosyl group (in which the —R-moiety is formed by eliminating one hydrogen atom from the above —R group), and the examples include glucopyranosyloxy methyl, glucopyranosyloxy ethyl and glucopyranosyloxy propyl. The configuration of the glycosidic linkage can be an α or β configuration depending on the stereochemistry of constituent monosaccharides, and thus both D isomers and L isomers are included in the present invention.

As used herein, the alkyl group, the alkenyl group, the alkynyl group, the alkoxy group, the alkoxycarbonyl group, the acyloxy group, the amino group, the alkylamino group, the alkylthio group, the cycloalkyl group, the heterocycloalkyl group, the aryl group and the heteroaryl group may be substituted or unsubstituted unless otherwise specified. The term "substitute" refers to replacing one or more hydrogen atoms by one or more substituents which may be the same or different from each other. Examples of the substituent include, but are not limited to, a halogen group (for example, F, Cl, Br or I), a hydroxyl group, an amino group, a cyano group, a nitro group, a mercapto group, an alkoxycarbonyl group, an acyloxy group, an amide group, a carboxy group, an alkanesulfonyl group, an alkylcarbonyl group, a carbamide group, a carbamyl group, a carboxyl group, a thioureido group, a thiocyanate group, a sulfonamide group, an alkyl group, an alkenyl group, an alkynyl group, an alkyloxy group, an aryl group, a heteroaryl group, a cycloalkyl group and a heterocyclylalkyl group. In the above, an alkyl group, an alkenyl group, an alkynyl group, an alkyloxy group, an aryl group, a heteroaryl group, a heteroaryloxy group, an alkylamino group, an arylamino group, an oxo group (O═), a thioxo group (S═), a thio group, a silyl group, an alkylthio group, an arylthio group, an alkylsulfonyl group, an arylsulfonyl group, an acylamino group, an aminoacyl group, an aminothioacyl group, an amidino group, a thioureido group, a thiocyanate group, a sulfonamide group, a guanidine group, a ureido group, an acyl group, a thioacyl group, a carbamyl group (—C(O)NH$_2$), a carboxyl group (—COOH) and a carboxylic acid ester, and in the above, an alkyl group, an alkenyl group, an alkynyl group, an alkyloxycarbonyl group, an aryl group, a heteroaryl group, a cyclyl group and a heterocyclyl group may also be substituted. The cycloalkyl group, the cycloalkenyl group, the heterocycloalkyl group, the heterocycloalkenyl group, the aryl group and the heteroaryl group may join together in any combination to form a condensed ring. The substituent(s) can be protected by a protecting group during a synthesis process. The "protecting group" as used herein refers to a group or moiety used to protect or mask the functionality which may cause an unwanted reaction during process steps. The protecting group can prevent such a reaction from occurring during the steps, after which the removal of the protecting group allows the original functionality to be presented. Examples of the protecting group include, but are not limited to, a trimethylsilyl group (TES), a tert-butyloxycarbonyl group (tBoc), a benzyloxycarbonyl group (CBZ) and a 9-fluorenylmethyloxycarbonyl group (Fmoc).

The pterosin derivative of the present invention include not only a pterosin compound itself but also, if applicable, a salt thereof, a prodrug thereof and a solvate thereof. For example, the salt can be formed by a reaction between an anion and a positively-charged group (for example, an amino group) on a pterosin compound. Suitable examples of such a salt include hydrochlorides, hydrogen bromides, hydrogen iodides, sulfates, nitrates, phosphates, citrates, methanesulfonates, trifluoroacetates, acetates, malates, sulfonates, tartrates, fumarates, glutamates, glucuronates, lactates, glutarates and maleates. Similarly, the salt can be formed by a reaction between a cation and a negatively-charged group (for example, a carboxylate group) on a pterosin compound. Suitable examples of such a salt include sodium salts, potassium salts, magnesium salts, calcium salts and ammonium salts such as tetramethylammonium salts. Also, quaternary nitrogen atom-containing salts of pterosin compounds are included. Examples of the prodrug include esters and other pharmaceutically acceptable compounds which can provide an active pterosin compound after administered to a subject. The solvate refers to a complex formed from an active pterosin compound and a pharmaceutically acceptable solvent. Examples of the pharmaceutically acceptable solvent include water, ethanol, isopropanol, ethyl acetate, acetic acid and ethanolamine.

The pterosin derivative used in the present invention may be a naturally-occurring, chemical synthetic or semisynthetic compound. Examples of the naturally-occurring pterosin derivative include, but are not particularly limited to, the one extracted from bracken belonging to the family Dennstaedtiaceae, Pteridaceae or the like. The extraction of the desired compound from bracken may be performed according to a known method, a method known per se, or a modified method thereof (see Yoshihira K et al., Chem. Pharm. Bull., 19, 1491-1495 (1971), for example). Examples of the semisynthetic pterosin derivative include, but are not particularly limited to, a compound obtained by deglycosylation of ptaquiloside, known as a bracken extract, and subsequent addition of a desired substituent; and a compound obtained by addition of a desired substituent to indene. The addition of a substituent may be performed according to a known method, a method known per se, or a modified method thereof. In addition, the pterosin derivative used in the present invention can be obtained by another method as well, for example, the synthesis method as described in Mohamed A et al., Molecules, 17, 5795-5802 (2012).

The pterosin derivative of the present invention can be administered directly or as a pharmaceutical composition obtainable by mixing with a pharmacologically acceptable carrier, excipient, diluent, etc. into an appropriate dosage form, whether orally or parenterally (e.g. as injections). Preferred is direct administration by intra-articular injection.

The composition for oral administration may be in a solid or liquid dosage form, and the specific examples include tablets (including sugar-coated tablets and film-coated tablets), pills, granules, powders, capsules (including soft capsules), syrups, emulsions and suspensions. The composition for parenteral administration may be in the form of an injection, a suppository or the like, and examples of the injection may include injections for intra-articular administration. These preparations are produced by a well-known method using an additive shown below. Examples of the additive include excipients (for example, organic excipients including lactose, sucrose, glucose, and sugar derivatives such as mannitol and sorbitol; corn starch, potato starch, and starch derivatives such as α starch and dextrin; cellulose derivatives such as crystalline cellulose; gum arabic; dextran; and pullulan; and inorganic excipients including light anhydrous silicic acid and silicate derivatives such as synthetic aluminum silicate, calcium silicate and magnesium aluminometasilicate; phosphates such as calcium hydrogen phosphate; carbonates such as calcium carbonate; and sulfates such as calcium sulfate), lubricants (for example, stearic acid and metal stearates such as calcium stearate and magnesium stearate; talc; colloidal silica; waxes such as beeswax and spermaceti wax; boric acid; adipic acid; sulfates such as sodium sulfate; glycol; fumaric acid; sodium benzoate; DL-leucine; lauryl sulfates such as sodium lauryl sulfate and magnesium lauryl sulfate; silicic acid derivatives such as silicic acid anhydride and silicic acid hydrate; and the above-listed starch and starch derivatives), binders (for example, hydroxypropyl cellulose, hydroxypropylmethyl cellulose, polyvinyl pyrrolidone, macrogol and the same compounds as the above excipients), disintegrants (for example, cellulose derivatives such as low-substituted hydroxypropyl cellulose, carboxymethyl cellulose, calcium carboxymethyl cellulose and internally cross-linked sodium carboxymethyl cellulose; and chemically modified starches and/or celluloses such as carboxymethyl starch, sodium carboxymethyl starch and cross-linked polyvinyl pyrrolidone), emulsifiers (for example, colloidal clays such as bentonite and veegum; metal hydroxides such as magnesium hydroxide and aluminum hydroxide; anionic surfactants such as sodium lauryl sulfate and calcium stearate; cationic surfactants such as benzalkonium chloride; and nonionic surfactants such as polyoxyethylene alkyl ether, polyoxyethylene sorbitan fatty acid ester and sucrose fatty acid ester), stabilizers (for example, p-hydroxybenzoic acid esters such as methylparaben and propylparaben; alcohols such as chlorobutanol, benzyl alcohol and phenyl ethyl alcohol; benzalkonium chloride; phenols such as phenol and cresol; thimerosal; dehydroacetic acid; and sorbic acid), corrigents (for example, commonly used sweeteners, acidulants, flavors, etc.) and diluents.

In addition, the preparation of the present invention may be produced in the form of a sustained-release microsphere by, for example, a coacervation method, a melt extrusion method, a spray drying method, a solvent evaporation method or the like. Such a microsphere may be a double emulsion (water-in-oil-in-water (W/O/W)) or a single emulsion (oil-in-water (O/W)). The encapsulation of the pterosin derivative into microspheres may be performed by mixing a pterosin derivative-containing aqueous phase and an oil phase (for example, the method described in Japanese Patent No. 3765338); or by mixing an aqueous phase containing gelatin, agar, sodium alginate, polyvinyl alcohol or a basic amino acid (for example, arginine, histidine, lysine, etc.) and an oil phase, and bringing the resulting mixture into contact with a solution of the pterosin derivative (for example, the method described in JP-A 2005-206491).

The dose of the pterosin derivative in the present invention may vary with various conditions such as patient's symptoms, age and body weight, but in intra-articular administration, for example, the dose for an adult is in the range of 0.01 mg (preferably 0.05 mg) to 100 mg (preferably 50 mg) per administration and this amount can be administered once or more. The dose may be increased or reduced depending on the patient's symptoms.

The pterosin derivative of the present invention may be used in combination with autologous cartilage transplantation, stem cell-derived chondrocyte transplantation, etc.

Another aspect of the present invention includes a functional food comprising the above-described pterosin derivative for the treatment of a disease associated with cartilage loss, cartilage degeneration and/or cartilage thinning. Such a functional food is provided particularly for the treatment of osteoarthritis. The pterosin derivative may be derived from an extract solution of bracken belonging to the family Dennstaedtiaceae, Pteridaceae or the like, field horsetail belonging to the family Equisetaceae, or Scythian lamb belonging to the family Dicksoniaceae, or from a dried powder of the extract solution.

Examples of the pterosin derivative used in the present invention are shown in Table 1.

TABLE 1

| Compound | $R_1$ | $R_2$ | $R_3$ | $R_4$ | $R_5$ | $R_6$ | $R_7$ | $R_8$ |
|---|---|---|---|---|---|---|---|---|
| 1 | $CH_3$ | $CH_2OH$ | H | H | H | $CH_3$ | $CH_2CH_2OH$ | $CH_3$ |
| 2 | H | $CH_3$ | H | H | H | $CH_3$ | $CH_2CH_2OH$ | $CH_3$ |
| 3 | $CH_3$ | H | H | H | H | $CH_3$ | $CH_2CH_2OH$ | $CH_3$ |
| 4 | H | $CH_3$ | H | H | H | $CH_3$ | $C_2H_4COOH$ | $CH_3$ |
| 5 | H | $CH_3$ | H | H | H | $CH_3$ | $CH_2CH_2Cl$ | $CH_3$ |
| 6 | H | $CH_2OH$ | H | H | H | $CH_3$ | $CH_2CH_2OH$ | $CH_3$ |
| 7 | $CH_3$ | $CH_3$ | H | H | H | $CH_3$ | $CH_2CH_2Cl$ | $CH_3$ |
| 8 | $CH_3$ | $CH_3$ | H | H | H | $CH_3$ | $CH_2CH_2OCH_3$ | $CH_3$ |
| 9 | $CH_3$ | $CH_2OH$ | H | H | H | $CH_3$ | $CH_2CH_2Cl$ | $CH_3$ |
| 10 | $CH_3$ | OH | H | H | H | $CH_3$ | $CH_2CH_2OH$ | $CH_3$ |
| 11 | $CH_3$ | H | H | H | H | $CH_3$ | $CH_2CH_2OCH_3$ | $CH_3$ |
| 12 | H | $CH_3$ | H | H | H | $CH_3$ | $CH_2CH_2OCH_3$ | $CH_3$ |
| 13 | $CH_3$ | H | H | H | H | $CH_2OH$ | $CH_2CH_2OH$ | $CH_3$ |
| 14 | $CH_3$ | $CH_3$ | H | H | OH | $CH_3$ | $CH_2CH_2Cl$ | $CH_3$ |
| 15 | $CH_2OH$ | $CH_3$ | H | H | H | $CH_3$ | $CH_2CH_2OCH_3$ | $CH_3$ |
| 16 | $CH_3$ | $CH_3$ | H | H | H | $CH_3$ | $CH_2CH_2OH$ | $CH_3$ |
| 17 | $CH_3$ | $CH_2OH$ | H | H | H | $CH_3$ | $CH_2CH_2Oglu$ | $CH_3$ |
| 18 | $CH_3$ | $CH_2OH$ | H | H | H | $CH_3$ | $CH_2CH_2Oglu$ | $CH_3$ |
| 19 | $CH_3$ | $CH_2Oglu$ | H | H | H | $CH_3$ | $CH_2CH_2OH$ | $CH_3$ |
| 20 | H | $CH_3$ | H | H | H | $CH_3$ | $CH_2CH_2Oglu$ | $CH_3$ |
| 21 | $CH_3$ | H | H | H | H | $CH_3$ | $CH_2CH_2Oglu$ | $CH_3$ |
| 22 | $CH_3$ | H | H | Oglu | H | $CH_3$ | $CH_2CH_2OH$ | $CH_3$ |
| 23 | $CH_3$ | H | Oglu | H | H | $CH_3$ | $CH_2CH_2Oglu$ | $CH_3$ |
| 24 | $CH_3$ | $CH_3$ | H | Oglu | H | $CH_3$ | $CH_2CH_2OH$ | $CH_3$ |
| 25 | $CH_3$ | $CH_3$ | H | Oara | H | $CH_3$ | $CH_2CH_2Cl$ | $CH_3$ |
| 26 | $CH_3$ | $CH_2Oglu$ | H | H | H | $CH_3$ | $CH_2CH_2Oglu$ | $CH_3$ |
| 27 | $CH_3$ | $CH_2OH$ | H | Oara | H | $CH_3$ | $CH_2CH_2Oglu$ | H |
| 28 | H | $CH_3$ | H | Oglu | H | $CH_3$ | $CH_2CH_2Oglu$ | $CH_3$ |
| 29 | H | $CH_3$ | H | H | H | $CH_3$ | $CH_2CH_2OCH_3$ | $CH_3$ |
| 30 | $CH_3$ | H | H | H | H | $CH_2OH$ | $CH_2CH_2Oglu$ | $CH_3$ |
| 31 | $CH_3$ | H | H | H | OH | $CH_3$ | $CH_2CH_2Oglu$ | $CH_3$ |
| 32 | $CH_3$ | $CH_3$ | H | H | H | $CH_3$ | $CH_2CH_2Oglu$ | $CH_3$ |
| 33 | $CH_3$ | $CH_3$ | H | Oara | H | $CH_3$ | $CHOHCH_2OH$ | $CH_3$ |
| 34 | $CH_3$ | $CH_3$ | H | H | Oglu | $CH_3$ | $CH_2CH_2OH$ | $CH_3$ |
| 35 | $CH_3$ | H | $CH_3$ | Oglu | H | $CH_3$ | $CH_2CH_2OH$ | $CH_3$ |
| 36 | $CH_3$ | H | H | H | OH | $CH_3$ | $CH_2CH_2OH$ | $CH_3$ |
| 37 | $CH_3$ | $CH_2OH$ | H | H | OH | $CH_3$ | $CH_2CH_2OH$ | $CH_3$ |
| 38 | $CH_3$ | H | H | H | H | $CH_2CH_2OH$ | $CH_3$ | H |
| 39 | $CH_3$ | OH | H | H | H | $CH_3$ | $CH_3$ | $CH_3$ |
| 40 | $CH_3$ | $CH_3$ | H | H | H | $CH_3$ | $CH_2CH_2Oglu$ | $CH_3$ |
| 41 | $CH_3$ | $CH_3$ | H | 4cou-glu | H | $CH_3$ | $CH_2CH_2OH$ | $CH_3$ |
| 42 | $CH_3$ | $CH_3$ | 3glu | H | H | $CH_3$ | $CH_2CH_2OH$ | $CH_3$ |
| 43 | $CH_3$ | $CH_3$ | 6cou-glu | H | H | $CH_3$ | $CH_2CH_2OH$ | $CH_3$ |
| 44 | H | H | H | H | H | $CH_3$ | Br | $CH_3$ |
| 45 | $COOC_2H_5$ | H | H | H | H | $CH_3$ | Br | $CH_3$ |
| 46 | $COOC_2H_5$ | $CH_3$ | H | H | H | $CH_3$ | Br | $CH_3$ |
| 47 | $COOC_2H_5$ | $CH_3$ | H | H | H | $CH_3$ | $C=CH_2$ | $CH_3$ |
| 48 | $CH_2OTES$ | $CH_3$ | H | H | H | $CH_3$ | $CH_2CH_2TIPSO$ | $CH_3$ |
| 49 | H | $CH_2OH$ | H | H | H | $CH_3$ | $CH_2CH_2OCH_3$ | $CH_3$ |
| 50 | $CH_3$ | $CH_3$ | H | H | OH | $CH_3$ | $CH_2CH_2OH$ | $CH_3$ |
| 51 | $CH_3$ | $CH_3$ | H | H | OH | $CH_3$ | $CH_2CH_2OCH_3$ | $CH_3$ |

In the table, glu stands for glucose, ara stands for arabinose, 4cou-glu stands for 4-O-p-coumaroyl-D-glucose, 3glu stands for 3-O-β-D-glucopyranoside, 6cou-glu stands for 6-O-p-coumaroyl-D-glucose, TES stands for a triethylsilyl group, and TIPSO stands for a triisopropylsilyloxy group.

Hereinafter, the present invention will be illustrated in more detail by examples, but is not limited thereto.

EXAMPLES

Example 1

<Pterosin B>

In the experiments, a pterosin B extracted from bracken (hereinafter, referred to as extracted pterosin B) (available from Research Center for Medicinal Plant Resources, the National Institute of Biomedical Innovation) and a pterosin B synthesized chemically (hereinafter, referred to as synthesized pterosin B) (available from intellim Corporation) were used.

<Effects of Extracted Pterosin B in Mouse Chondrocytes>

Figure 1B:
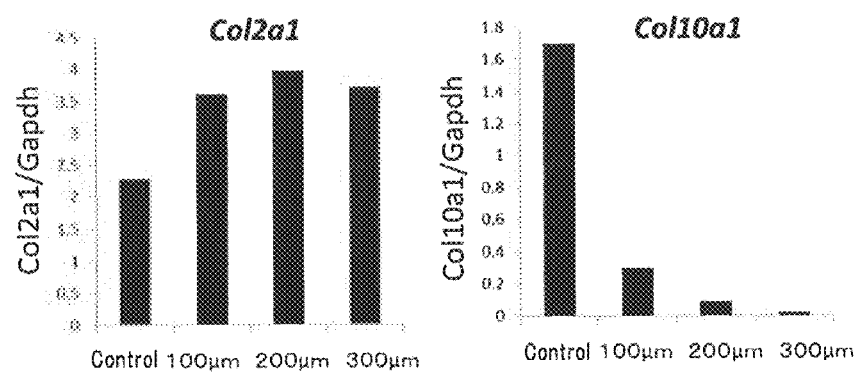
FIG. 1B shows the results of quantitative PCR of Col2a1 and Col10a1 in wild-type mouse primary chondrocytes cultured in the presence of a vehicle control (DMSO) or various concentrations of pterosin B.

Primary chondrocytes obtained from the distal femoral epiphyseal cartilage and the proximal tibial epiphyseal cartilage of 1- to 5-day-old mice were pelletized by centrifugation, and to the cell pellet, the extracted pterosin B at a given concentration (0 μM (only DMSO as a vehicle), 100 μM, 200 μM or 300 μM) was added in DMEM supplemented with 10% fetal calf serum. The cell pellet was collected 28 days after the addition of the extracted pterosin B, and then stained with safranin O. As a result, it was shown that the staining intensity increased with increasing concentration of the extracted pterosin B (FIG. 1A). In addition, the mRNA amounts of Col2a1, Col10a1 and Sik3 relative to Gapdh in the cell pellet were measured by quantitative RT-PCR. As a result, the amount of Col2a1 mRNA increased with increasing concentration of the extracted pterosin B, while the amount of Col10a1 mRNA decreased with increasing concentration of the extracted pterosin B (FIG. 1B). Col2a1 is a gene relevant to osteoblasts (cells responsible for bone formation in bone tissues), and Col10a1 is a gene indicative of hypertrophic differentiation of chondrocytes.

<Effects of Pterosin B on Embryonic Mouse Metatarsal Bone Growth>

Figure 2:
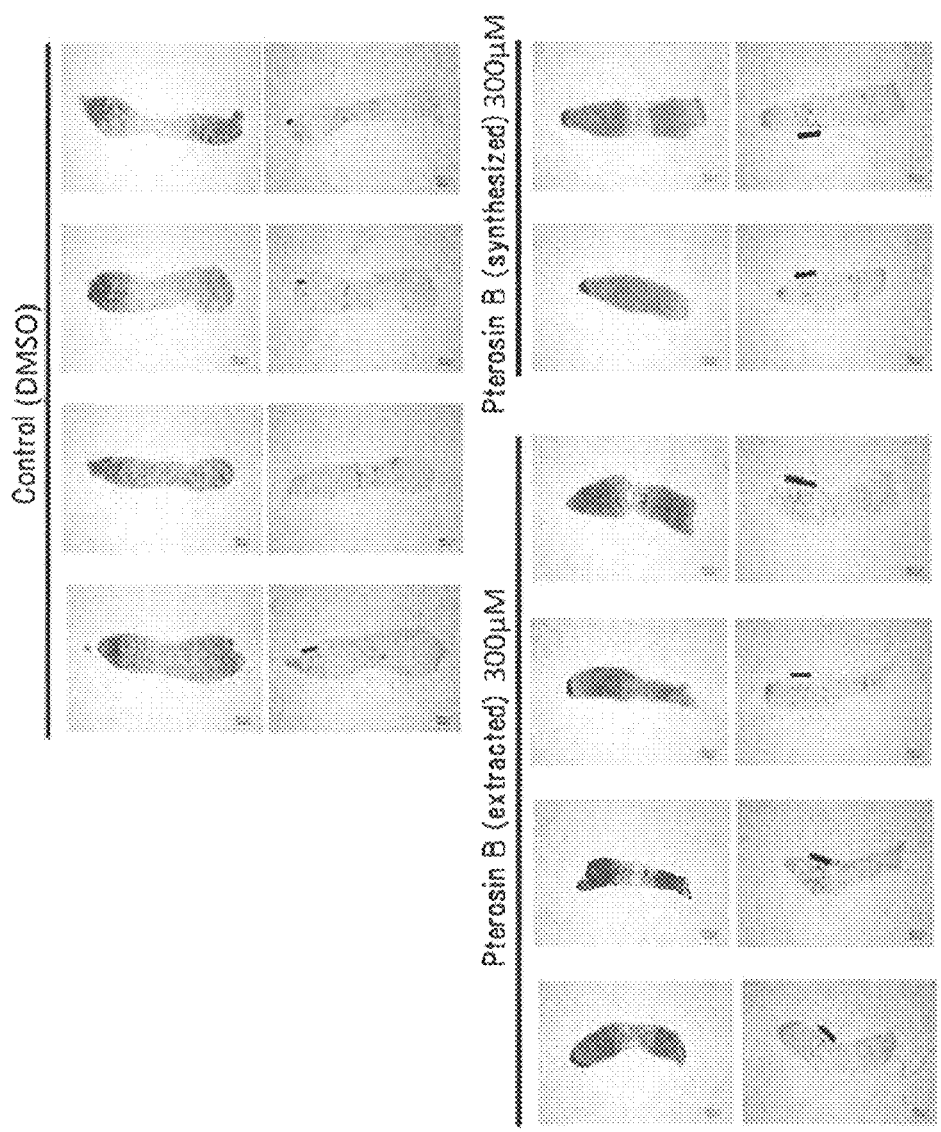
FIG. 2 shows images of safranin O staining and BrdU staining in embryonic mouse metatarsal bone tissue-cultured in the presence of a vehicle control (DMSO), synthesized pterosin B or extracted pterosin B. In each panel, the bar represents the location of proliferating chondrocytes.
Figure 3A:
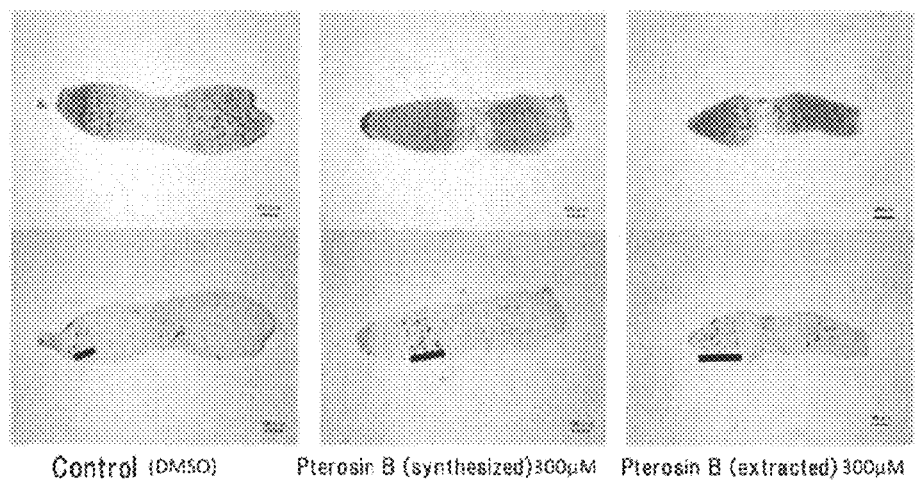
FIG. 3A shows typical images of safranin O staining and BrdU staining in embryonic mouse metatarsal bone tissue-cultured in the presence of a vehicle control (DMSO), synthesized pterosin B or extracted pterosin B. In each panel, the bar represents the location of proliferating chondrocytes.
Figure 3B:
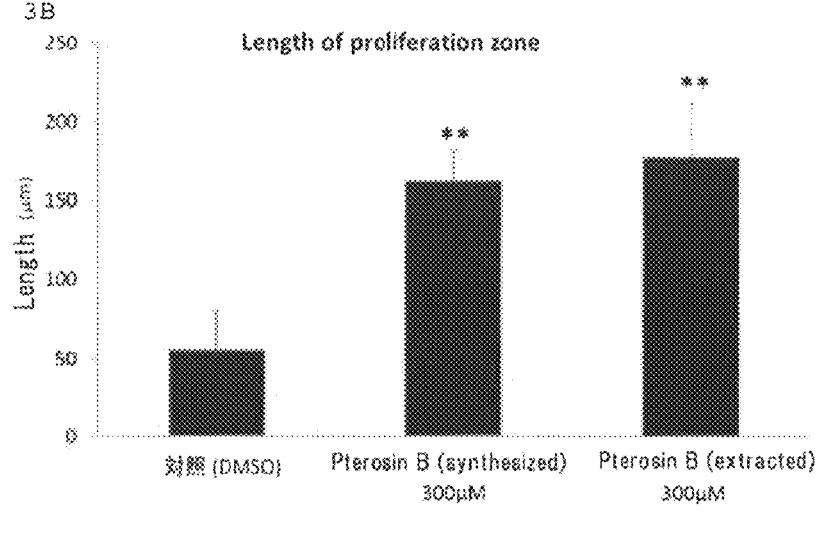
FIG. 3B shows a graph quantifying the length of the proliferating chondrocyte zone.

The metatarsal bone was isolated from a mouse embryo of E15.5, and tissue culture of the bone was performed in DMEM supplemented with 10% fetal calf serum. To the culture medium, 300 μM of the extracted pterosin B or the synthesized pterosin B was added, and the culture was further continued. Seven days later, the metatarsal bone was collected and its histological sections were prepared. At 8 hours before the collection of the metatarsal bone, BrdU was added to the culture medium. The histological sections of the metatarsal bone were stained with safranin O and immunostained with an anti-BrdU antibody. As a result, it was shown that, in the presence of the extracted pterosin B or the synthesized pterosin B, the safranin O-stained area and the BrdU-positive cell number were increased (FIGS. 2 and 3). Meanwhile, the number of hypertrophic chondrocytes was decreased in the presence of the extracted pterosin B or the synthesized pterosin B (FIG. 4). These results showed that the extracted pterosin B and the synthesized pterosin B are comparable in the proliferative effect on chondrocytes and the inhibitory effect on chondrocyte hypertrophy.

<Effects of Pterosin B in Human Chondrocytes>

Figure 5A:
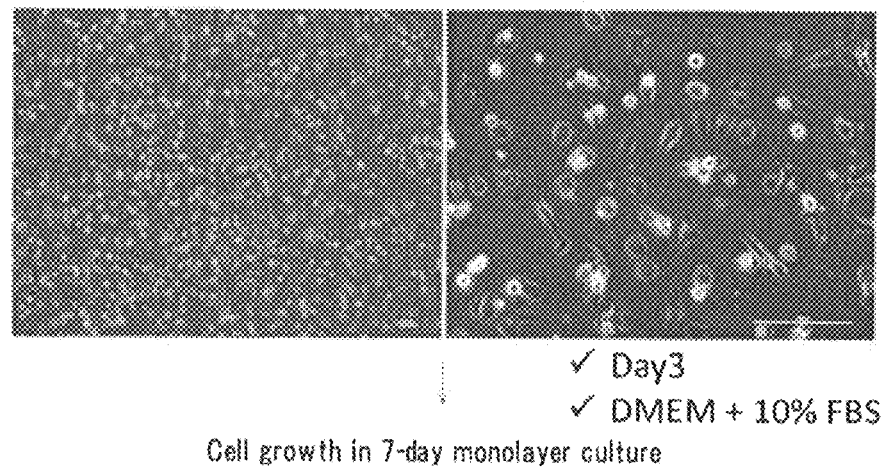
FIG. 5A shows phase contrast images of 3-day cultured human primary chondrocytes and the scheme of pellet preparation.
Figure 5B:
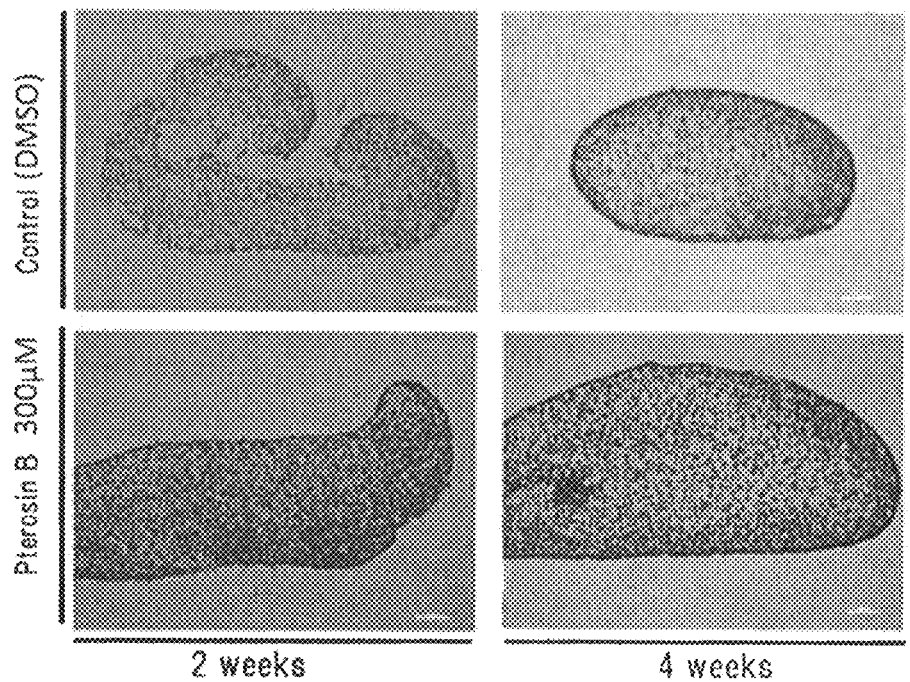
FIG. 5B shows images of safranin O staining in human primary chondrocytes pellet-cultured in the presence of a vehicle control (DMSO) or pterosin B for 2 or 4 weeks.
Figure 6:
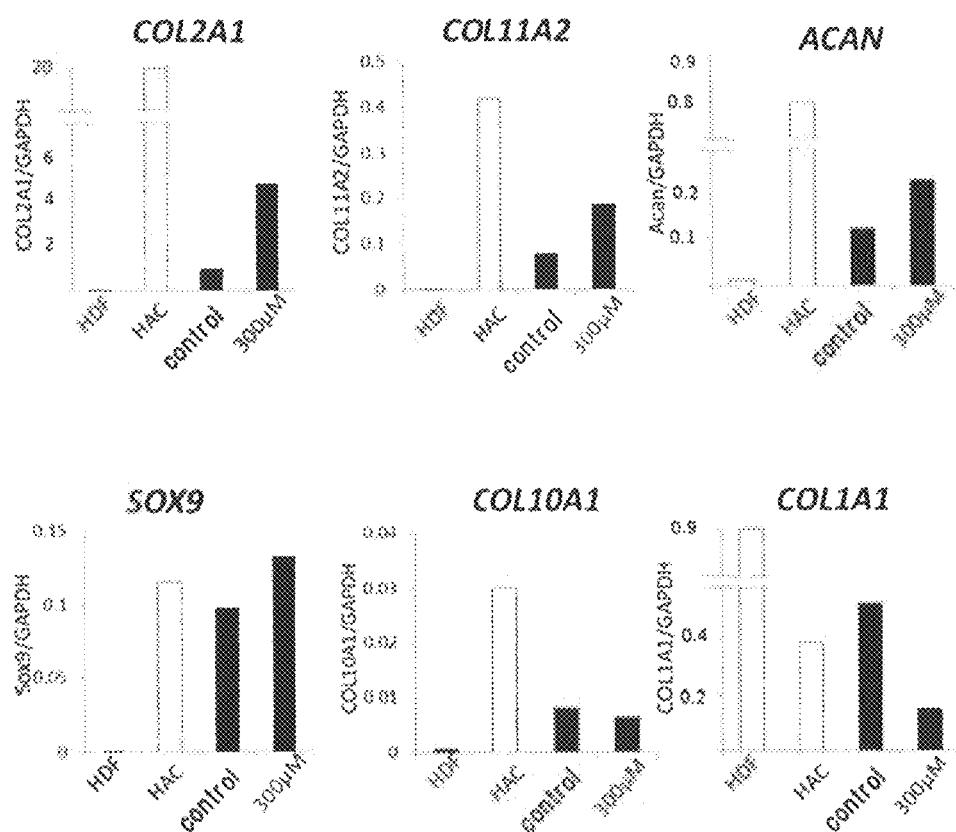
FIG. 6 shows the results of quantitative PCR of COL2A1, COL11A2, ACAN, SOX9, COL10A1 and COL1A1 in human primary chondrocytes pellet-cultured in the presence of a vehicle control (DMSO) or pterosin B for 2 weeks as well as in human fibroblasts (HDFs) and human articular chondrocytes (HACs).

Chondrocytes collected from a 68-year-old woman with medial compartmental idiopathic osteonecrosis under informed consent were cultured in DMEM (Dulbecco's Modified Eagle's Medium) supplemented with 10% fetal calf serum for 7 days (an image of a 3-day culture is shown in FIG. 5A), and then pelletized by centrifugation (FIG. 5A). The human chondrocyte pellet was cultured in DMEM supplemented with 10% fetal calf serum and 300 μM of the extracted pterosin B for 14 or 28 days. The cell pellet was collected and then stained with safranin O. As a result, it was shown that the staining intensity in the presence of the extracted pterosin B was increased on and after 14 days from the addition of the extracted pterosin B (FIG. 5B). In addition, the mRNA amounts of COL2A1, COL11A2, ACAN, SOX9, COL10A1 and COL1A1 relative to GAPDH in the cell pellet were measured by quantitative RT-PCR. As a result, the mRNA amounts of COL2A1, COL11A2, ACAN and SOX9 were increased by the addition of the synthesized pterosin B, while the mRNA amounts of COL10A1 and COL1A1 were decreased by the addition of the extracted pterosin B (FIG. 6). These results showed that pterosin B increases production of cartilage matrices such as COL2A1 by human chondrocytes and inhibits hypertrophy of human chondrocytes. Therefore, pterosin B is considered to have the effect of promoting hyaline cartilage growth in humans as well.

<In Vivo Effects of Pterosin B>

As shown in Table 2, 300 μM or 900 μM of the extracted pterosin B or a vehicle (a mixed solution of PBS and DMSO) was administered into the lateral side of the left knee articular cavity in 8-week-old male C57BL/6 mice 3 times a week.

TABLE 2

| No. | Left | Right | Findings of medial femoral epicondyle |
| --- | --- | --- | --- |
| 1 | PBS-DMSO | Non-treated | Mild loss of cartilage |
| 2 | PBS-DMSO | Non-treated | Mild loss of cartilage |
| 3 | PBS-DMSO | Non-treated | No apparent abnormalities |
| 4 | 300 μM | Non-treated | No apparent abnormalities |
| 5 | 300 μM | Non-treated | Moderate osteoarthritis |
| 6 | 300 μM | Non-treated | No apparent abnormalities |
| 7 | 300 μM | Non-treated | No apparent abnormalities |
| 8 | 900 μM | Non-treated | No apparent abnormalities |
| 9 | 900 μM | Non-treated | No apparent abnormalities |
| 10 | 900 μM | Non-treated | Moderate osteoarthritis and chondroma |
| 11 | 900 μM | Non-treated | No apparent abnormalities |

After the administration was continued for 4 weeks, the knee joint was dissected and then stained with safranin O/fast green/iron hematoxylin. As shown in FIG. 7A, in the region between the baseline along the direction of the bone and the other line running at 90 degrees to the baseline, the area of the articular cartilage on the medial femoral epicondyle was measured by computer-assisted analysis. Typical images are shown in FIG. 7B. The measurement results showed that the cartilage area increased with increasing concentration of pterosin B (FIG. 7C). Other findings are shown in Table 1. These results showed that in vivo administration of pterosin B into the knee articular cavity also has the effect of promoting cartilage growth.

Example 2

<Pterosin Derivatives>

Onitin (1), 14-O-methylonitin (2), 14-deoxy-14-chloroonitin (pterosin R) (3), 14-O-methylpterosin G (4), pterosin Z and pterosin I (5) were extracted from bracken (available from Research Center for Medicinal Plant Resources, the National Institute of Biomedical Innovation). The structural formula of each compound is shown below.

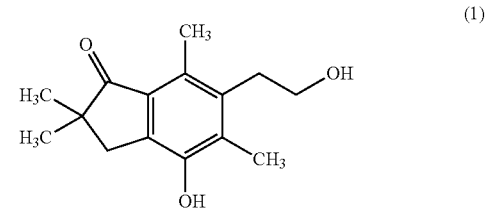 [SMILES: Cc1c(O)c2c(c(C)c1CCCl)C(=O)C(C)(C)C2]

(1)

-continued

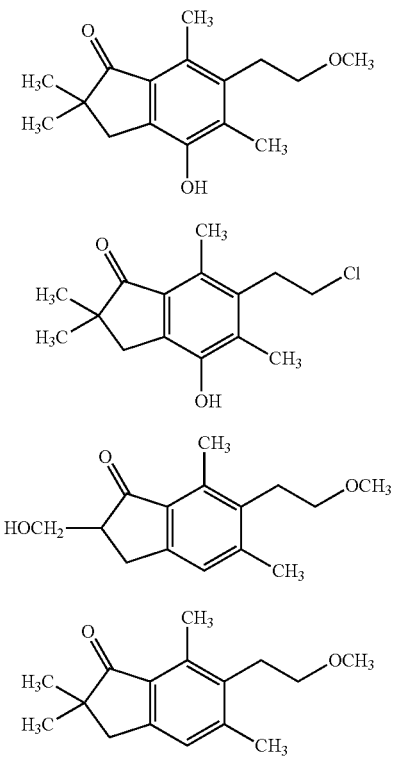

<Measurement of SIK3 Inhibitory Activities of Pterosin Derivatives>

Figure 8:
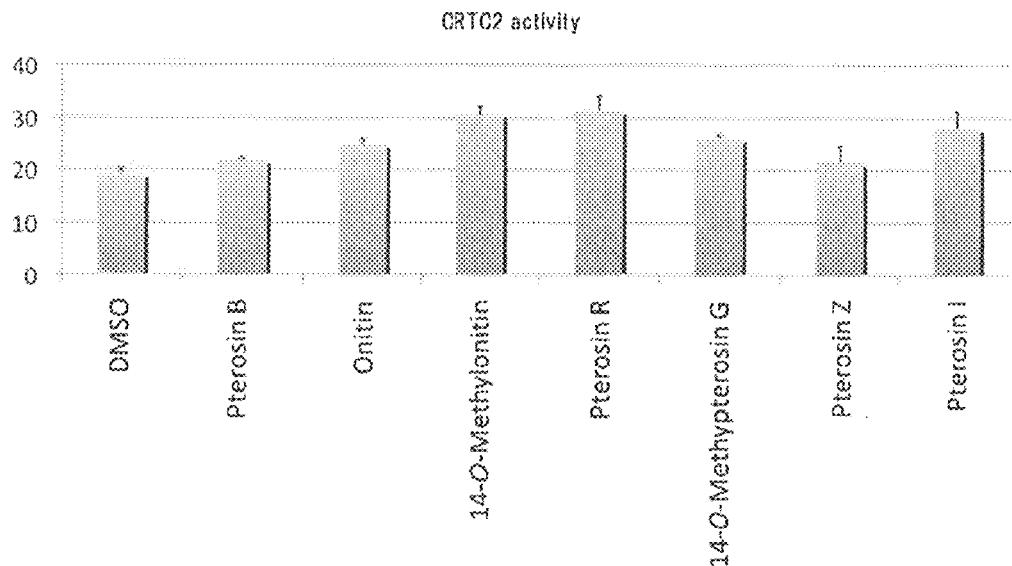
FIG. 8 shows the CRTC2 activities of several chemicals (DMSO, pterosin B, onitin, 14-O-methylonitin, pterosin R, 14-O-methylpterosin G, pterosin Z and pterosin I) determined as a measure of SIK3 inhibitory activity. DMSO was used as a vehicle control.

Comparative evaluation of pterosin derivatives was performed in terms of the inhibitory effect on SIK3 signaling. As a measure of the SIK3 inhibitory activity, the induced activity of the transcription coupling factor CRTC2 (which is also referred to as TORC2, serves as a coupling factor of the transcription factor CREB, and is an inhibition target of SIK3) was measured according to the method described in PCT/JP2012/063709. At the concentration of 150 μM, at which pterosin B can slightly inhibit SIK3, several pterosin B analogs (onitin, 14-O-methyl-onitin, 14-chloro-onitin, 14-O-methyl-pterosin G, pterosin Z and pterosin I) were found to be highly active than pterosin B (FIG. 8). These results indicated that onitin, 14-O-methyl-onitin, 14-chloro-onitin, 14-O-methyl-pterosin G, pterosin Z and pterosin I are likely to have the same effect of promoting cartilage growth as pterosin B has.

<Effects of Pterosin Derivatives on Chondrogenesis>

Figure 9:
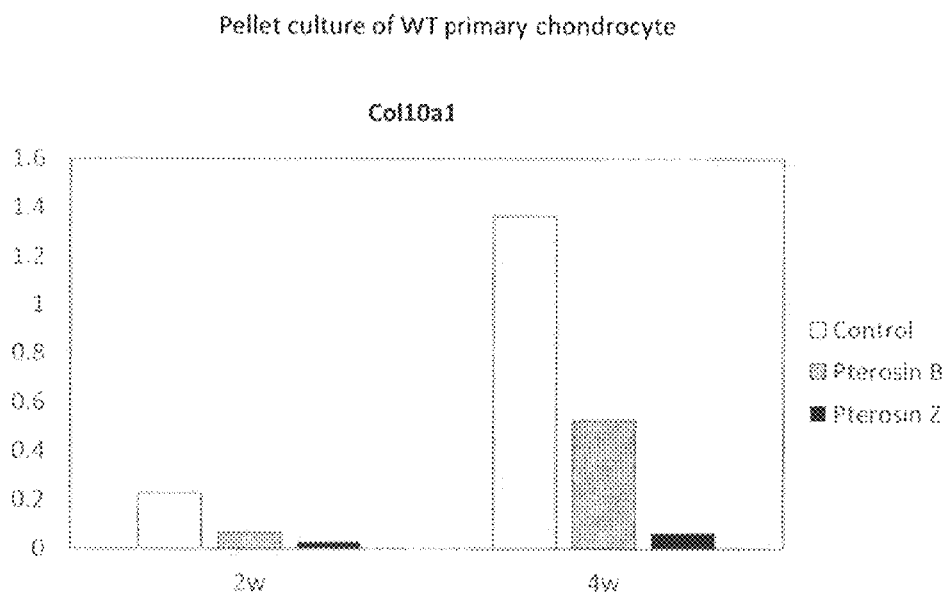
FIG. 9 shows the results of quantitative PCR of Col10a1 in wild-type mouse primary chondrocytes cultured in the presence of a vehicle control (DMSO), pterosin B or pterosin Z.

In the same manner as in Example 1, primary chondrocytes obtained from 1- to 5-day-old mice were pelletized, and to the cell pellet, a pterosin derivative (synthesized pterosin B or pterosin Z) at 300 μM was added in DMEM supplemented with 10% fetal calf serum. At 2 or 4 weeks after the addition, the cell pellet was collected and the mRNA amount of Col10a1 relative to Gapdh was measured by quantitative RT-PCR. As a result, it was shown that Col10a1 was decreased by the addition of pterosin Z as well as the addition of the synthesized pterosin B (FIG. 9). These results showed that pterosin Z has the same inhibitory effect on chondrocyte hypertrophy as pterosin B has.

INDUSTRIAL APPLICABILITY

The present invention enables the treatment of a disease associated with cartilage loss, cartilage degeneration and/or cartilage thinning.

The invention claimed is:

1. A method for treating cartilage loss, cartilage degeneration, cartilage thinning or osteoarthritis by inhibiting SIK3, comprising a step of administering a pterosin compound having SIK3 inhibitory activity of formula (II)

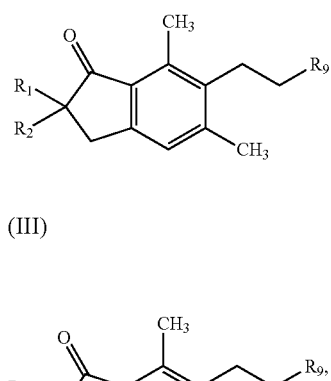

or formula (III)

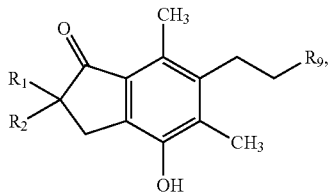

wherein $R_1$ and $R_2$ are each independently hydrogen, a methyl group or a hydroxymethyl group, and $R_9$ is a hydroxy group, a methoxy group or chlorine, or a pharmaceutically acceptable salt thereof, to a patient.

2. The method according to claim 1, wherein the pterosin compound having SIK3 inhibitory activity is a compound of formula (IV):

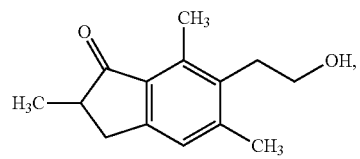

formula (V):

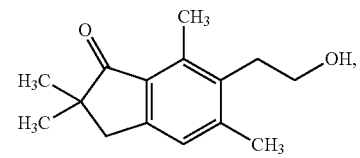

formula (VI):

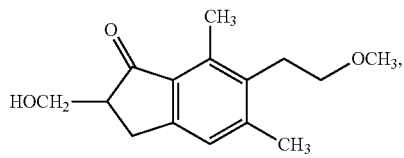

formula (VII):
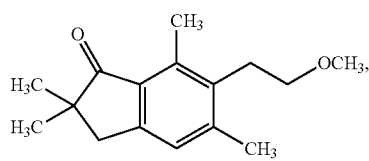
formula (VIII):
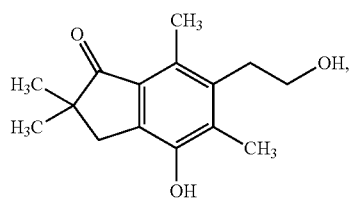
formula (IX):
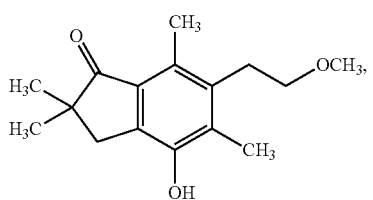
or formula (X):
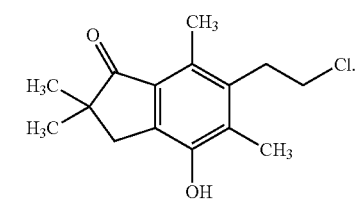
* * * * *